United States Patent [19]

Mikami et al.

[11] 4,010,206
[45] Mar. 1, 1977

[54] METHOD FOR PRODUCING CYCLOHEXANONE AND ALKYL-SUBSTITUTED OR UNSUBSTITUTED PHENOL

[75] Inventors: Ichiro Mikami, Chiba; Sadao Danno, Ichihara; Izuhiko Uchida, Ichihara; Yasutaka Tasaki, Ichihara; Junichi Kugimoto, Ichihara; Satoru Fujitsu, Yamaguchi, all of Japan

[73] Assignee: UBE Industries, Ltd., Ube, Japan

[22] Filed: Jan. 22, 1976

[21] Appl. No.: 651,455

[30] Foreign Application Priority Data

Jan. 31, 1975 Japan .............................. 50-12349

[52] U.S. Cl. ..................... 260/586 P; 260/621 G
[51] Int. Cl.² .............. C07C 27/12; C07C 37/00; C07C 45/02
[58] Field of Search .................. 260/586 P, 621 G

[56] References Cited

UNITED STATES PATENTS

| | | | |
|---|---|---|---|
| 2,380,675 | 7/1945 | Rust et al. | 260/586 P |
| 3,360,572 | 12/1967 | Selwitz | 260/621 G |
| 3,846,499 | 11/1974 | Riedl | 260/621 C |

FOREIGN PATENTS OR APPLICATIONS

| | | | |
|---|---|---|---|
| 1,506,296 | 12/1967 | France | 260/586 P |
| 237,160 | 2/1969 | U.S.S.R. | 260/586 P |

OTHER PUBLICATIONS

Redoshkin et al., "Trudy pokhim. i Khim. Tekhnol.", 3, No. 1, 3–8 (1960) C.A. 56:1367f.
Rummel et al., "J. Prakt. Chem," 37(3–4), 206–213, (1968) C.A. 68:77413y.
Schiketanz et al., "Rev. Roum. Chim", 1968, 13(10), 1385–1390, CA. 70:67806f.
Farberov et al, "Miflekhumuya", 1969, 9(1), 107–115 CA 71:21755f.
"Uki. Khim. Zh", 30, 1073–1075 (1976).

*Primary Examiner*—Norman Morgenstern

[57] ABSTRACT

Both cyclohexanone and alkyl-substituted or unsubstituted phenol are simultaneously produced, in a one step reaction, by oxidizing, in the liquid phase, an alkyl-substituted or unsubstituted phenylcyclohexane of the formula (I):

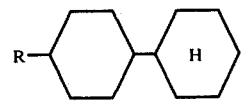

(I)

wherein R represents either a hydrogen atom or a methyl radical with an oxidizing gas containing molecular oxygen therein in the presence of hydrogen bromide.

18 Claims, No Drawings

METHOD FOR PRODUCING CYCLOHEXANONE AND ALKYL-SUBSTITUTED OR UNSUBSTITUTED PHENOL

The present invention relates to a method for producing cyclohexanone and alkyl-substituted or unsubstituted phenol. More particularly, the present invention relates to a method for producing, in a one step reaction, cyclhexanone and alkyl-substituted or unsubstituted phenol by oxydizing, in the liquid phase, alkyl-substituted or unsubstituted phenylcyclohexane.

In view of Ukr. Khim. Zh. 30, 1073–1075 (1965), a conventional method for producing cyclohexanone and alkyl-substituted or unsubstituted phenol includes a first step in which said alkyl-substituted or unsubstituted phenylcyclohexane (which will be referred to as phenylcyclohexane compound hereinafter) is oxidized to produce the corresponding phenylcyclohexylperoxide compound, and a second step wherein said corresponding phenylcyclohexylperoxide compound is acid decomposed to produce cyclohexanone and the corresponding phenol compound. However, the above-mentioned two-step method is disadvantageous with regard to the following points. That is, the two step reactions result in operational complications. Also, since the reaction velocity of the first step oxidation is very low, a high concentration of the corresponding phenylcyclohexylperoxide compound can not be obtained in a short time. Further, even in the second step acid decomposition, the resultant cyclohexanone and corresponding phenol compound can not be produced at a high percentage of selectivity. (This term will be clarified hereinafter).

The object of the present invention is to provide a method for producing cyclohexanone and alkyl-substituted or unsubstituted phenol by a one step reaction in a short time with high selectivity.

The above-mentioned object can be attained by the method of the present invention which comprises oxidizing, in the liquid phase, an alkyl-substituted or unsubstituted phenylcyclohexane of the formula (I):

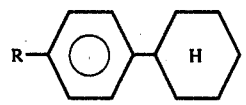

wherein R represents either a hydrogen atom or a methyl radical by bringing an oxidizing gas containing molecular oxygen into contact with said alkyl-substituted or unsubstituted phenyl-cyclohexane in the presence of hydrogen bromide, and isolating and resultant cyclohexanone and alkyl-substituted or unsubstituted phenol from the oxidation mixture.

The phenylcyclohexane compound of formula (I) is either phenylcyclohexane or p-toluylcyclohexane.

The phenylcyclohexane compound usable as a starting material for the method of the present invention can be produced, for example, by hydrogenation of the corresponding alkyl-substituted or unsubstituted diphenyl with hydrogen in the presence of a hydrogenation catalyst by alkylation of the corresponding alkyl-substituted or unsubstituted benzene with cyclohexene or by condensation of the corresponding alkyl-substituted or unsubstituted benzene with cyclohexanol or halogenated cyclohexane. The phenylcyclohexane may be produced by the method of British Pat. No. 1,184,022.

It is not required that the phenylcyclohexane compound to be used as a starting material for the present invention be completely refined before the oxidation step. However, it is preferable that the starting material is washed beforehand with an acid solution and, then, with an alkali solution and, thereafter, rectified in order to reduce the impurity content of the starting material.

The method of the present invention is effected in the presense of hydrogen bromide as a catalyst. The hydrogen bromide in the form of gas may be directly added into the oxidation mixture. The hydrogen bromide may first be dissolved in the starting material or in an organic solvent, and then, the solution may be mixed into the oxidation mixture. Otherwise, the hydrogen bromide may be generated by adding an inorganic bromide salt, for example, NaBr, KBr and $CaBr_2$, or organic acid bromide, for example, acetyl bromide and benzoyl bromide, into an oxidation mixture containing an acid, for example, hydrogen chloride.

The oxidation mixture may contain therein a hydrogen halide other than the hydrogen bromide, for example, hydrogen chloride, since said hydrogen halide does not have a bad influence upon the oxidation of the starting material. Particularly, the hydrogen chloride is cheaper and more stable than hydrogen bromide in the oxidation mixture, and can maintain the oxidation mixture acidic throughout the oxidation period. Accordingly, the hydrogen chloride may be added in an optional amount, for example, up to supersaturation, into the oxidation mixture.

Preferably, the hydrogen bromide is present in an amount of at least 0.01%, more preferably, 0.1 to 10%, based on the weight of the starting phenylcylohexane compound in the oxidation mixture. A too large amount of the hydrogen bromide in the oxidation mixture may lead to undesirable side reactions and result in an economical disadvantage.

The oxidation mixture may contain therein a small amount of a radical reaction initiator, for example, azobisisobutylonitrile, laurylperoxide, benzoylperoxide or tert-butylhydroperoxide. The amount of the initiator is not limited in any way. However, it is preferable that the initiator is contained in an amount of 0.01 to 10% based on the weight of the starting phenylcylohexane compound therein.

In the process of the present invention, the starting pehnylcyclohexane compound which is a liquid, may be brought into direct contact with the oxidizing gas. Otherwise, the starting phenylcyclohexane compound may be dissolved in an organic solvent inert under the oxidation conditions of the method of the present invention, and the solution may be subjected to the oxidation process. The organic solvent may be selected from the group consisting of aromatic hydrocarbons, for example, benzene, toluene and o, m and p-xylenes, halogenated hydrocarbons, for example, ethylene dichloride and tetrachloromethane, and aliphatic carboxylic acids, for example, acetic acid and propionic acid. Generally, the starting phenylcylohexane compound is preferably dissolved in a concentration of 5 to 100% in the inert organic solvent.

In the method of the present invention, the oxidation is preferably effected at a temperature of −30° to 100° C more preferably, 0° to 80° C. Oxidation at a temperature lower than −30° C is not good because it causes a low oxidation velocity. Also, oxidation at a temperature higher than 100° C is not welcome because it causes undesirable side reactions which results in a decrease in the selectivity of the resultant cyclohexanone and phenol compound.

There is no limitation to the amount of pressure under which the oxidation of the present invention is effected. That is, oxidation may be performed either under an ambient pressure, a reduced pressure or an increased pressure as long as the oxidation can be effected in the liquid phase and as long as the necessary amount of oxygen can be supplied into the oxidation mixture.

In the method of the present invention, the oxidizing gas may consist of pure (industrially pure) oxygen gas, air or a mixture gas of oxygen gas and at least one inert gas, for example, nitrogen gas. The oxidizing gas usuable for the method of the present invention preferably includes therein at least 1.0% by mole of molecular oxygen.

In the performance of the method of the present invention, the starting phenylcyclohexane compound or its solution in an inert organic solvent is received in a closed vessel, for example, an autoclave, and the hydrogen bromide and, if necessary, the hydrogen chloride in the form of gas or solution are charged into the closed vessel so as to dissolve into the starting phenylcyclohexane compound or its solution. Thereafter, the oxidizing gas is introduced into the closed vessel so that the oxidizing gas comes into contact with the starting phenylcyclohexane compound while the oxidation mixture is stirred, shaken or bubbled and while the oxidation mixture is maintained at a desired temperature and pressure.

After the completion of the oxidation reaction, the resultant phenol compound and cyclohexanone are isolated from the oxidation mixture by a known method. For example, the oxidation mixture is neutralized by the addition of an alkali solution, for example, sodium hydroxide solution, thereto so as to convert the hydrogen bromide and, if necessary, the hydrogen chloride to non-volatile salts. Thereafter, the neutralized mixture is subjected to distillation so as to separate the resultant cyclohexane and phenol compound and the residual phenylcyclohexane compound from each other.

When the oxidation mixture contains the resultant cyclohexanone and phenol, a portion of said resultant cyclohexanone is distilled, and an azeotropic mixture of the resultant phenol and the remaining cyclohexanone is then azeotropically separated from the oxidation mixture. Thereafter, the residual phenolcyclohexane is distilled. Said separated azeotropic is subjected to an extractive distillation using an extracting reagent, for example, glycol compounds and glycerol, in order to separate the cyclohexanone from the phenol.

However, when p-cresol and cyclohexanone are produced, since they do not form the azeotropic mixture, they and the residual p-cyclohexyltoluene can be separately distilled from the oxidation mixture at different temperatures from each other.

By the above-mentioned method of the present invention, both the cyclohexanone and the alkyl-substituted or unsubstituted phenol can be simultaneously produced from the alkyl-substituted or unsubstituted phenylcyclohexane by a one step reaction in a short time.

The following specific examples will serve to more fully explain the practice of the present invention.

However, it should be understood that these are only examples and in no way limit the present invention.

In the examples, the terms "selectivity percentage" and "yield percentage" refer to percentages calculated in accordance with the following equations 1 and 2, respectively.

$$\text{selectivity percentage} = \frac{Y}{X_2 - X_1} \times 100 \quad (1)$$

$$\text{yield percentage} = \frac{Y}{X_2} \times 100 \quad (2)$$

wherein $Y$ represents an amount in m mole of the resultant product, that is, phenol or p-cresol or cyclohexanone, $X_1$ represents a residual amount in m mole of the starting material, that is, phenylcyclohexane or p-cyclohexyltoluene after the oxidation reaction is completed, and $X_2$ represents an initial amount in m mole of the starting material subjected to the oxidizing reaction.

EXAMPLE 1

A solution of a starting material was prepared by charging 5 ml (29.0 m mole) of phenylcyclohexane and 20 ml of ethylene dichloride into an autoclave provided with a thermometer, a stirrer and a cooler and having an internal volume of 100 ml. After the autoclave was air-tight, hydrogen bromide was blown thereinto to such an extent that the concentration thereof in the solution became 0.09 mole/l, and hydrogen chloride was blown into the autocalve to such an extent that the concentration thereof became 0.38 mole/l. Thereafter, industrially pure oxygen gas was blown into said autoclave under a pressure of 11 atmospheres for 10 minutes while the oxidation mixture was maintained at a temperature of 35° C by cooling and while stirring the oxidation mixture. After the oxidizing reaction was completed, the resultant phenol and cyclohexanone and the residual phenylcyclohexane were respectively separated from the oxidation mixture by the following method.

The oxidation mixture was subjected to distillation at a temperature of 84° C under an ambient pressure in order to separate ethylene dichloride. A portion of the resultant cyclohexanone was separated from the residue of the oxidation mixture by distillation at a temperature of 85° to 87° C under a reduced pressure of 88 mmHg. Next, the distillation residue of the oxidation mixture was subjected to an azeotropic distillation at a temperature of 82 to 90° C under a reduced pressure of 26 mmHg so as to separate an azeotropic mixture consisting of the resultant phenol and the remaining portion of cyclohexanone. Thereafter, the residual phenolcyclohexane was distilled from the above distillation residue at a temperature of 99° to 100° C under a reduced pressure of 15 mmHg. The azeotropic mixture obtained above was mixed with 1,4-butanediol in a weight of five times that the azeotropic mixture. The mixture was first distilled at a temperature of 27° C under a reduced pressure of 5 mmHg to separate cyclohexanone and then distilled at a temperature of 62° C under the same reduced pressure as above, to separate phenol.

The resultant phenol and cyclohexanone were obtained in amounts of 15.1 m mole (yield percentage=52.2 and selectivity percentage=97.1) and 14.0 m mole (yield percentage=48.4 and selectivity percentage=91.1).

EXAMPLE 2

The same autoclave as used in Example 1 was charged with 5 ml (29.1 m mole) of phenyl-cyclohexane and 20 ml of ethylene dichloride to prepare a solution. After the autoclave was closed and air-tight, hydrogen bromide was blown into the autoclave to such an extent that the concentration thereof in the solution became 0.17 mole/l. Thereafter, industrially pure oxygen gas was blown into the autoclave under a pressure of 10 atmospheres for 10 minutes while maintaining the oxidation mixture in the autoclave at a temperature of 30° C by cooling and while said oxidation mixture was stirred. After completion of the oxidizing reaction, the resultant phenol and cyclohexanone and the residual phenylcyclohexane were separated from each other by the same method as in Example 1. The resultant phenol and cyclohexanone were obtained in amounts of 11.9 m mole (selectivity percentage=74.5 and yield percentage=41.1) and 7.83 m mole (selectivity percentage=48.8 and yield percentage=26.9%), respectively.

EXAMPLE 3

In order to prepare the solution of a starting material, the same autoclave used in Example 1 was charged with 5 ml (29.1 m mole) of phenylcyclohexane and 20 ml of benzene. After said autoclave was closed, hydrogen bromide was blown thereinto to such an extent that the concentration thereof in the solution became 0.13 mole/l, and hydrogen chloride to such an extent that the concentration thereof in the solution became 0.39 mole/l. Thereafter, industrially pure oxygen gas was blown into the solution under a pressure of 10 atmospheres for 10 minutes while maintaining the oxidation mixture at a temperature of 25° C by cooling and while said oxidation mixture was stirred. The resultant phenol and cyclohexanone and the residual phenylcyclohexane were separated from the oxydation mixture by the same method as in Example 1. The resultant phenol and cyclohexanone were obtained in amounts of 7.92 mole (selectivity percentage=40.2 and yield percentage=27.2) and 1.43 m mole (selectivity percentage=7.2% and yield percentage=4.9%). It was observed that the resultant oxidation product further contained 2.7 m mole of adipic acid and 10.1 m mole of phexylcyclohexane.

EXAMPLE 4

The same autoclave as used in Example 1 was charged with 5 ml (29.1 m mole) of phenylcyclohexane and 20 ml of ethylene dichloride in order to prepare a starting material solution. After the autoclave was closed, hydrogen bromide was blown into the solution to such an extent that its concentration in the solution became 0.31 mole/l, and hydrogen chloride to such an extent that its concentration in the solution became 0.09 mole/l. Thereafter, air was blown into the solution under an ambient pressure for 26 minutes while the oxidation mixture was cooled and stirred at a temperature of 35° C. The resultant products and the residual phenylcyclohexane were separated from the oxidation mixture by the same method as in Example 1. The resultant phenol and cyclohexanone were obtained in amounts of 10.0 m mole (selectivity percentage=86.8 and yield percentage=34.5) and 6.97 m mole (selectivity percentage=60.5 and yield percentage=24.0), respectively.

EXAMPLE 5

The same autoclave as used in Example 1 was charged with 5 ml (29.1 m mole) of phenylcyclohexane and 20 ml of ethylene dichloride in order to prepare a solution of the starting material. After the autoclave was closed, hydrogen bromide was blown into the solution to such an extent that its concentration in the solution became 0.99 mole/l, and hydrogen chloride to such an extent that its concentration in the solution became 0.66 mole/l. Thereafter, industrially pure oxygen gas was blown into the solution under a pressure of 11 atmospheres for 5 min. while stirring and maintaining the oxidation mixture at a temperature of 65° C. The oxidation product included 8.88 m mole (selectivity percentage=75.2 and yield percentage=30.3) of phenol, 3.78 m mole (selectivity percentage=32.0 and yield percentage=12.9%) of cyclohexanone and 0.75 m mole of adipic acid.

EXAMPLE 6

The same autoclave as used in Example 1 was charged with 4.60g (26.4 m mole) of p-cyclohexyl-toluene and 25g of ethylene dichloride to prepare a solution. After said autoclave was closed, hydrogen bromide was blown into the solution to such an extent that its concentration in the solution became 0.1 mole/l, and hydrogen chloride was blown into the solution to such an extent that its concentration in the solution became 0.1 mole/l. Thereafter, industrially pure oxygen gas was blown into the solution at a pressure of 10 atmospheres for 22 minutes while the oxidation mixture was stirred and maintained at a temperature of 55° C. It was determined that 2.16g (12.4 m mole) of p-cyclohexyltoluene were consumed and 1.19g (11.0 m mole) of p-cresol and 0.90g (9.24 m mole) of cyclohexanone were obtained. That is, the selectivity percentage and the yield percentage of the resultant p-cresol were 88.8 and 41.9, respectively, and those of the resultant cyclohexanone were 74.4 and 34.9.

EXAMPLE 7

The same autoclave as used in Example 1 was charged with 4.64g of a mixture of 15.2 m mole of p-cyclohexyltoluene and the balance of o-cyclohexyltoluene and 25g of ethylene dichloride to prepare a solution. After closing the autoclave, hydrogen bromide was blown into the solution to such an extent that its concentration in the solution became 0.1 mole/l and hydrogen chloride was introduced into the solution to such an extent that its concentration in the solution became 0.1 mole/l. After that, industrially pure oxygen gas was introduced into the solution under a pressure of 10 atmospheres for 8 minutes while stirring and maintaining the oxidation mixture of a temperature of 55° C. It was determined that the initial amount of o-cyclohexyltoluene was substantially not consumed, 5.59 m mole of p-cyclohexyltoluene were consumed, and the resultant product included 0.50g (4.64 m mole, selectivity percentage=83.1 and yield percentage=30.5) of p-cresol and 0.41g (4.18 m mole, selectivity percentage=74.9 and yield percentage=27.6) of cyclohexanone.

EXAMPLE 8

The same autoclave as used in Example 1 was used to prepare a solution from 4.60g (26.4 m mole) of p-cyclohexyltoluene and 17g of benzene. After closing the autoclave, hydrogen bromide was introduced into the solution so that the concentration thereof in the solution was adjusted to 0.15 mole/l. Thereafter, air was introduced into the solution under a pressure of 15 atmospheres for 20 minutes while stirring and maintaining the oxidation mixture at a temperature of 55° C. It was determined that 2.00g (11.4 m mole) of p-cyclohexyltoluene were consumed and p-cresol and cyclohexanone were respectively obtained in amount of 0.97g (8.98 m mole, yield percentage=34.0, selectivity percentage=79.0) and 0.84g (8.53 m mole, yield percentage=32.3 and selectivity percentage=75.0).

What is claimed is:

1. A method for producing cyclohexanone and alkyl-substituted or unsubstituted phenol, comprising oxidizing, in the liquid phase, an alkyl-substituted or unsubstituted phenylcyclohexane of the formula (I):

(I)

wherein R represents either a hydrogen atom or a methyl radical by bringing an oxidizing gas containing molecular oxygen into contact with alkyl-substituted or unsubstituted phenylcyclohexane in the presense of hydrogen bromide, and isolating the resultant cyclohexanone and alkyl-substituted or unsubstituted phenol from the oxidation mixture.

2. A method as claimed in claim 1, wherein said hydrogen bromide is in an amount of at least 0.01% based on the weight of said alkyl-substituted or unsubstituted phenylcyclohexane.

3. A method as claimed in claim 2, wherein said amount of hydrogen bromide is between 0.1 and 10% based on the weight of said alkyl-substituted or unsubstituted phenylcylohexane.

4. A method as claimed in claim 1, wherein said oxidation mixture contains therein hydrogen chloride.

5. A method as claimed in claim 4, wherein said oxidizing mixture is supersaturated with said hydrogen chloride.

6. A method as claimed in claim 1, wherein said oxidation mixture contains therein a radical reaction initiator.

7. A method as claimed in claim 6, wherein said radical reaction initiator is selected from the group consisting of azobisiobutylonitrile, laurylperoxide, benzoylperoxide and tert-butylhydroperoxide.

8. A method as claimed in claim 1, wherein said alkyl-substituted or unsubstituted phenylcyclohexane is dissolved in an organic solvent inert under the oxidizing condition.

9. A method as claimed in claim 8, wherein said inert organic solvent is selected from the group consisting of aromatic hydrocarbons, halogenated hydrocarbons and aliphatic carboxylic acids.

10. A method as claimed in claim 9, wherein said aromatic hydrocarbon is selected from the group consisting of benzene, toluene and o;m- and p-xylenes.

11. A method as claimed in claim 9, wherein said halogenated hydrocarbon is either ethylene dichloride or tetrachloromethane.

12. A method as claimed in claim 9, wherein said aliphatic carboxylic acid is either acetic acid or propionic acid.

13. A method as claimed in claim 8, wherein the concentration of said alkyl-substituted or unsubstituted phenylcyclohexane in said organic solvent is at least 5% by weight.

14. A method as claimed in claim 1, wherein said oxidation is carried out at a temperature of −30° to 100° C.

15. A method as claimed in claim 14, wherein said oxidation temperature is between 0° and 80° C.

16. A method as claimed in claim 1, wherein said oxidizing gas consistis of pure oxygen, air or a mixture of oxygen and at least one inert gas.

17. A method as claimed in claim 1, wherein said molecular oxygen in said oxidizing gas is in an amount of at least 1% by mole.

18. A method as claimed in claim 1, wherein said oxidation mixture is stirred, shaken or bubbled during the oxidation operation.

* * * * *